United States Patent
Romanato et al.

(10) Patent No.: US 9,110,021 B2
(45) Date of Patent: Aug. 18, 2015

(54) SENSITIVITY ENHANCEMENT IN GRATING COUPLED SURFACE PLASMON RESONANCE BY AZIMUTHAL CONTROL

(75) Inventors: Filippo Romanato, Trieste (IT); Gianluca Ruffato, Padua (IT); Chee Cheong Wong, Singapore (SG); Lee Kwang Hong, Singapore (SG); Husen Kartasamita Kang, Singapore (SG)

(73) Assignee: Universita degli Studi di Padova, Padova (IT)

( * ) Notice: Subject to any disclaimer, the term of this patent is extended or adjusted under 35 U.S.C. 154(b) by 30 days.

(21) Appl. No.: 13/255,612

(22) PCT Filed: Mar. 8, 2010

(86) PCT No.: PCT/IB2010/000510
§ 371 (c)(1),
(2), (4) Date: Sep. 9, 2011

(87) PCT Pub. No.: WO2010/103386
PCT Pub. Date: Sep. 16, 2010

(65) Prior Publication Data
US 2012/0002203 A1    Jan. 5, 2012

Related U.S. Application Data

(60) Provisional application No. 61/158,940, filed on Mar. 10, 2009.

(51) Int. Cl.
*G01N 21/552* (2014.01)

(52) U.S. Cl.
CPC .................... *G01N 21/553* (2013.01)

(58) Field of Classification Search
CPC ............. G01N 21/553; G01N 21/774; G01N 21/7743; G01N 21/211; G01J 4/00
USPC ................... 356/369, 445–446, 364
See application file for complete search history.

(56) References Cited

U.S. PATENT DOCUMENTS

5,229,833 A * 7/1993 Stewart ........................ 356/364
5,442,448 A * 8/1995 Knoll ........................... 356/445

(Continued)

FOREIGN PATENT DOCUMENTS

WO     2008/057000 A1    5/2008

OTHER PUBLICATIONS

Romanato F et al: "Azimuthal dispersion and energy mode condensation of grating-coupled surface plasmon polaritons" Physical Review B (Condensed Matter and Materials Physics) American Physical Society by AIP USA, vol. 77, No. 24, Jun. 15, 2008, pp. 245435-2-245435-7.

(Continued)

*Primary Examiner* — Kara E Geisel
(74) *Attorney, Agent, or Firm* — Bryan W. Bockhop; Bockhop & Associates, LLC

(57) ABSTRACT

A method and a system for the enhancement of the sensitivity in surface plasmon resonance (SPR) sensors based metallic grating by exploiting the conical configuration is presented. We consider the propagation of surface plasmon polaritons (SPPs) excited by light from the visible to infrared spectrum range, incident on a plasmonic grating at different directions by varying both the zenith and azimuthal angles. For specific azimuthal angles, SPPs propagate in the grating plane perpendicular to the incident light momentum. This is the condition that allows increasing the number of different excited SPPs modes largely. We exploit this effect to increase the sensor sensitivity with the change of refractive index of thin film on the plasmonic grating surface. Polarization effects also contribute to a further modes enhancement and increase the sensitivity. A scheme for a lab-on-chip implementation of a system that allows a parallel detection in microfluidic channels has been shown.

5 Claims, 11 Drawing Sheets

(56) References Cited

U.S. PATENT DOCUMENTS

| | | | |
|---|---|---|---|
| 5,598,267 A * | 1/1997 | Sambles et al. | 356/369 |
| 5,925,878 A * | 7/1999 | Challener | 250/225 |
| 6,277,653 B1 * | 8/2001 | Challener et al. | 356/367 |
| 6,625,336 B2 * | 9/2003 | Challener et al. | 385/12 |
| 6,653,152 B2 * | 11/2003 | Challener | 436/518 |
| 6,982,792 B1 * | 1/2006 | Woollam et al. | 356/369 |
| 7,973,933 B2 * | 7/2011 | Homola et al. | 356/445 |
| 8,094,316 B1 * | 1/2012 | Homola et al. | 356/445 |
| 2002/0135780 A1 * | 9/2002 | Budach et al. | 356/521 |
| 2004/0142482 A1 * | 7/2004 | Westphal et al. | 436/164 |
| 2004/0155309 A1 * | 8/2004 | Sorin et al. | 257/433 |
| 2006/0106557 A1 * | 5/2006 | Fontaine et al. | 702/87 |

OTHER PUBLICATIONS

Donghyun Kim: "Effect of the azimuthal orientation on the performance of grating-coupled surface-plasmon resonance biosensors" Applied Optics Opt. Soc. America USA, vol. 44, No. 16 Jun. 1, 2005; pp. 3218-3223.

* cited by examiner

SENSITIVITY ENHANCEMENT IN GRATING COUPLED SURFACE PLASMON RESONANCE BY AZIMUTHAL CONTROL

CROSS-REFERENCE TO RELATED APPLICATION(S)

This application claims the benefit of U.S. Provisional Patent Application Ser. No. 61/158,940, filed Mar. 10, 2009, the entirety of which is hereby incorporated herein by reference.

This application claims the benefit of Patent Application No. PCT/IB2010/000510, filed Mar. 08, 2010, the entirety of which is hereby incorporated herein by reference.

BACKGROUND OF THE INVENTION

1. Field of the Invention

The invention relates to surface plasmon resonance sensors based on plasmonic grating and sensitivity enhancement can be obtained after an azimuthal rotation of gratings. The method describes a device and procedure to exploit this higher sensitivity.

2. Description of the Related Art

Sensors are devices for detecting and measuring physical, chemical and biological quantities. Sensors can be grouped into electrical, optical and mechanical sensors in accordance with various detection mechanisms. First optical chemical sensors were based on the measurement of changes in absorption spectrum and were developed for the measurement of $CO_2$ and $O_2$ concentration. Since then a large variety of optical methods have been used in chemical sensors and biosensors including, spectroscopy (luminescence, phosphorescence, fluorescence, Raman), interferometry (white light interferometry, modal interferometry in optical waveguide structures), spectroscopy of guided modes in optical waveguide structures (grating coupler, resonant mirror), and surface plasmon resonance (SPR). This discovery deals with the last type of sensors and, in particular, describes a device and method for the enhancement of the index refraction sensitivity based on the control of azimuthal angle of rotation of 1D plasmonic gratings Surface plasmon polariton (SPP) is defined as an electromagnetic (photon) excitation that couples with the electrons oscillations (on thin metal film) and propagates as a wave (polariton) along the interface between a metal and a dielectric medium. Fields intensity decays exponentially from the surface with extension length of the same order of wavelength inside the dielectric medium and about one order shorter into the metal. Due to this phenomenon, SPPs are particularly sensitive to optical and geometrical properties of the surface, e.g. shape, profile, roughness, refractive indices, and reveal themselves as a useful tool for surface analysis. These light-matter interactions and sensitivity due to the field enhancement are extensively used for chemo- or bio- sensing purposes. The resonant condition for excitation of surface plasmons with an electromagnetic wave depends on refractive index of the dielectric in the proximity of the metal surface. Therefore, variations in the refractive index can be monitored from changes in the interaction between an electromagnetic wave and a surface plasmon.

SPP sensors typically measure shifts of surface plasmon resonance as a function of a change of a refractive index of analyte molecules or a chemo-optical transducing medium. In optical sensors, surface plasmons are usually optically excited with an electromagnetic wave in the visible or near infrared spectrum.

SPR sensors can be used also as highly sensitive refractometers and can also be applied for the study of biomolecules and their interactions and for detection of chemical and biological compounds. In these applications, SPR sensors are combined with bio/chemo recognition elements which specifically interact with an analyte (e.g., antibody, enzymes, DNA).

Currently, several groups are using different SPR approaches to detect the change of refractive index. A refractive index resolution better than $3\times10^{-7}$ RIU (refractive index units) has been developed by Liedberg and BIAcore using a Kretschmann configuration prism-coupled SPR (PC-SPR) sensor; this study also concluded that sensitivity is higher at short wavelength. Gaurav claimed an angular sensitivity from 94.46°/RIU to 204.41°/RIU based on changing the prism refractive index. Van Duyne and his coworkers, working on localized surface plasmon resonance (LSPR) of noble metal nano-particle arrays, reported a refractive index resolution of $5\times10^{-3}$ RIU. Perez-Juste and Yu used gold nanorods with an aspect ratio of 3 to build multiplex biosensors with a sensitivity of 400 nm/RIU. Although prism-based coupling methods provide the best refractive index resolution, they suffer from extremely cumbersome optical maintenance. Furthermore, the commercialized prism-based SPR instrument is very expensive and is not amenable to miniaturization and integration. A LSPR nanosensor is much cheaper than an SPR instrument and can be miniaturized, but it has much lower sensitivity. Sensing based on Au nanorod SPR is a new method; a systematic analysis of the sensitivity has not yet been presented and controlling the aspect ratio of nanorod is inconsistent and troublesome.

Another common way for SPR excitation is to use a metallic grating. Yoon and Cullen have proposed grating coupled SPR (GC-SPR), demonstrating a sensitivity of 440 nm/RIU or 100°/RIU, which is lower than prism-based coupler SPR. Most of the groups are using a two dimensional CCD array to collect the reflected light from the grating substrate, which provide a higher reflective index resolution of $\sim10^{-6}$ RIU and over 200 sensing channels. Recently, Homola's group demonstrated an SPR biosensor with a reflective index resolution of $3.5\times10^{-6}$ RIU by using the advantages of both long-range and short-range surface plasmon excited simultaneously on a diffraction grating. Most recently, Alleyne has demonstrated a higher sensitivity of 680°/RIU by bandgap-assisted GC-SPR, but this requires a prism to enhance incident light momentum for exploring the grating's bandgap region.

Recently, our group has shown that the number of excited SPP modes in GCSPR is related to the azimuthal angle of the grating.

A SPP spectroscopy method of in surface plasmon resonance sensors was described in patent US 2008/0144027 A1 and in patent US 2007/0279634 A1 exploiting SPP grating based sensors and also the rotation of the gratings but with a different detection approach. When SPP is excited at a particular incident wavelength or angle, a dip in reflectivity spectrum can be observed.

DETAILED DESCRIPTION OF THE INVENTION

Figure 1:
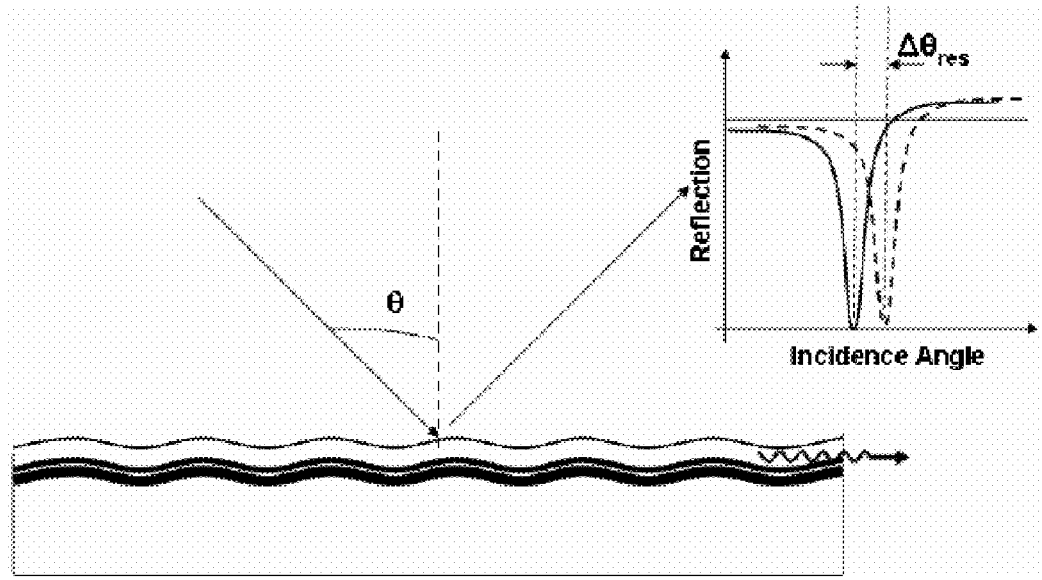
FIG. 1 depicts a method for SPR sensor detection using a sensor element on which a relief diffraction grating is prepared. On the diffraction grating, an electromagnetic wave is coupled to surface plasmons and is diffracted into a diverging beam. The diffracted beam is collected using CCD. The CCD can detect the diffracted beam in different wavelength.
Figure 2:
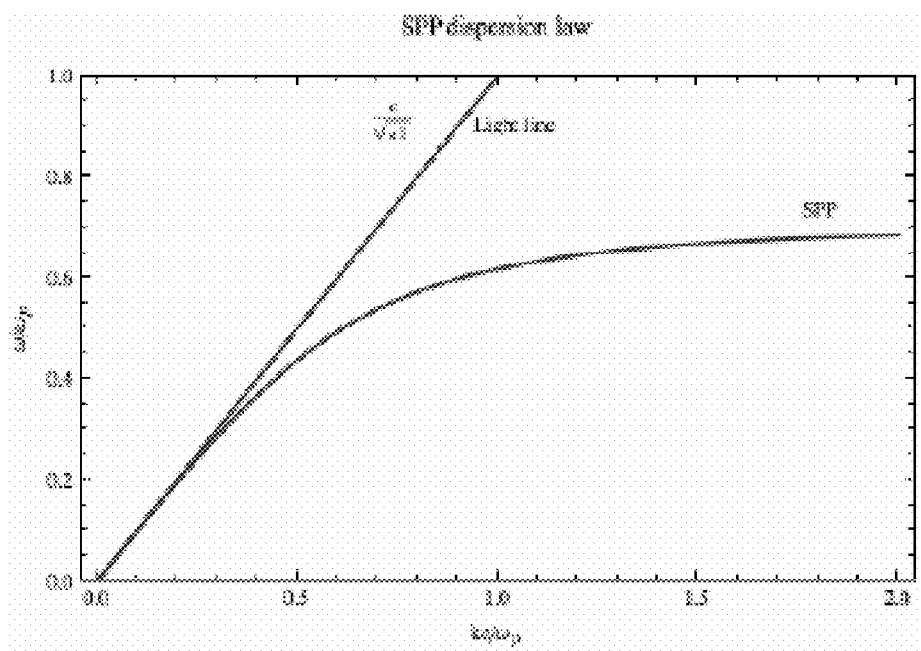
FIG. 2 is a comparison between SPPs dispersion curve and dispersion line of light in the dielectric medium

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Scientific Background

SPPs can be excited only in the frequency range wherein the real parts of the dielectric functions of the two media have opposite signs and the metal is opaque to radiation (negative real part of the dielectric constant). Commonly used metals are noble metals (Cu, Ag, Au) because free-electrons plasma model (Drude's Model) well explain dielectric function behaviour in the optical range. Assuming the validity of a Drude model for metal optical constants, SPPs propagating on a flat metal/dielectric interface are TM-polarized modes and the wave-vector $k_{spp}$ is given by the following expression:

$$k_\Phi SPP = 2\pi/(\sqrt{((\in_d \in_M)/(\in_d + \in_M))}) \quad (1)$$

where $\in_M$ and $\in_d$ are respectively the dielectric constants of the metal and of the dielectric medium, $\lambda$ is the illuminating wavelength in vacuum.

The dispersion curve of SPP ω(k) lies totally on the right of the light line (dispersion curve of light in the dielectric) and there is no matching between the two curves in the range of frequency that we are taking into account: SPPs have a non-radiative nature and once they have been generated, these modes propagate along the surface until energy is dissipated inside the metal. For the same reason, an incident light cannot excite SPPs because its momentum is greater than the incident light. The optical excitation of SPPs is possible only in such proper configurations that provide the matching between the incident light momentum and the SPP momentum. Two setups are suitable: prism coupling and grating coupling.

Prism coupling: the metallic film is sandwiched between the dielectric medium and the metal and a prism with a refractive index greater than the dielectric one is illuminated from the prism-side: since the prism is optically denser, incident momentum is increased and there exists an incident angle $\theta_{res}$ at which SPPs are excited:

$$k_\Phi SPP = 2\pi/\lambda n \sin[\theta_{res}] \quad (2)$$

where n is the prism refractive index, $\lambda$ is the incident wavelength in vacuum.

Grating coupling: metal surface is modulated by a periodic pattern. Incident light is diffracted and it is possible for a diffraction order to excite SPPs on the interface. Grating crystal momentum is exploited to sum to the incident light wave-vector and to realize the matching with SPP dispersion law. If Λ is the grating period, resonance condition is realized for the incident angle $\theta_{res}$, and the diffracted order n for which the resonance equation is satisfied (longitudinal incidence):

$$\theta_{res} + n\frac{2\pi}{\Lambda} \quad (3)$$

Figure 3:
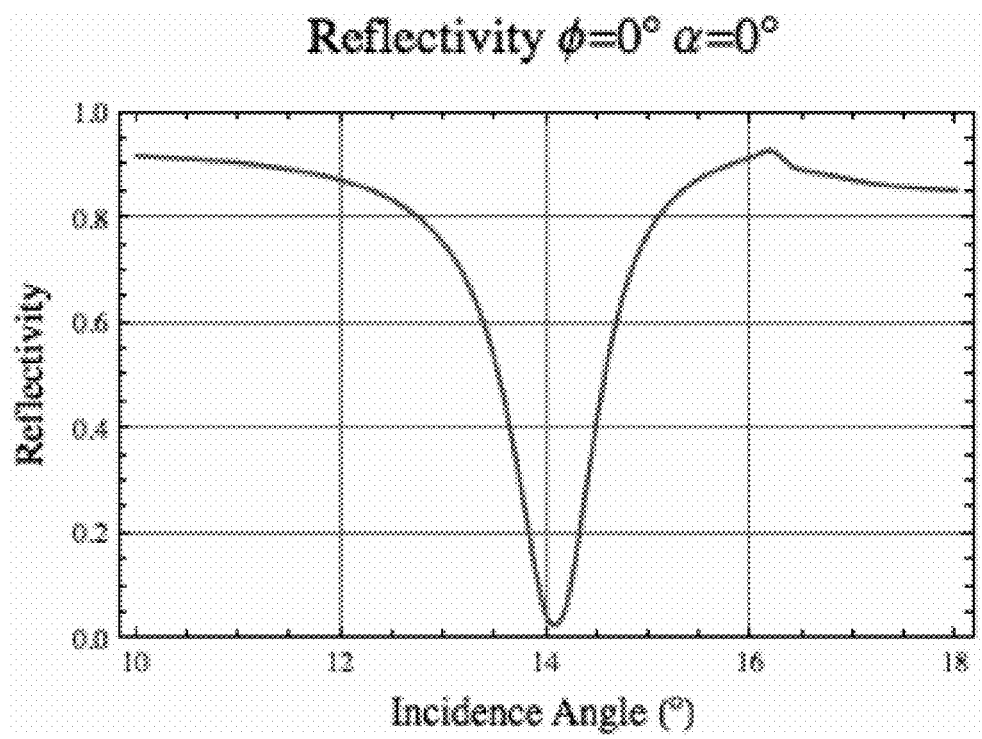
FIG. 3 is a simulated reflectivity spectrum for incident wavelength of 640 nm on a un-rotated Ag—Au (37 nm-7nm) grating with period and amplitude of 500 nm and 35 nm respectively. A dip in the reflectivity spectrum represented as surface plasmon excitation, and the incidence angle for the dip occurred is called resonance angle.

When surface plasmon polaritons are excited, a dip in reflectivity spectrum is observed at a particular incidence angle (the so called resonance angle) as shown in FIG. 3, since the illuminating energy is absorbed by the excited surface modes and propagates along the interface till it is dissipated by metal absorptions: thus the reflectivity goes to zero and a minimum appears in the reflectivity curve.

Figure 4:
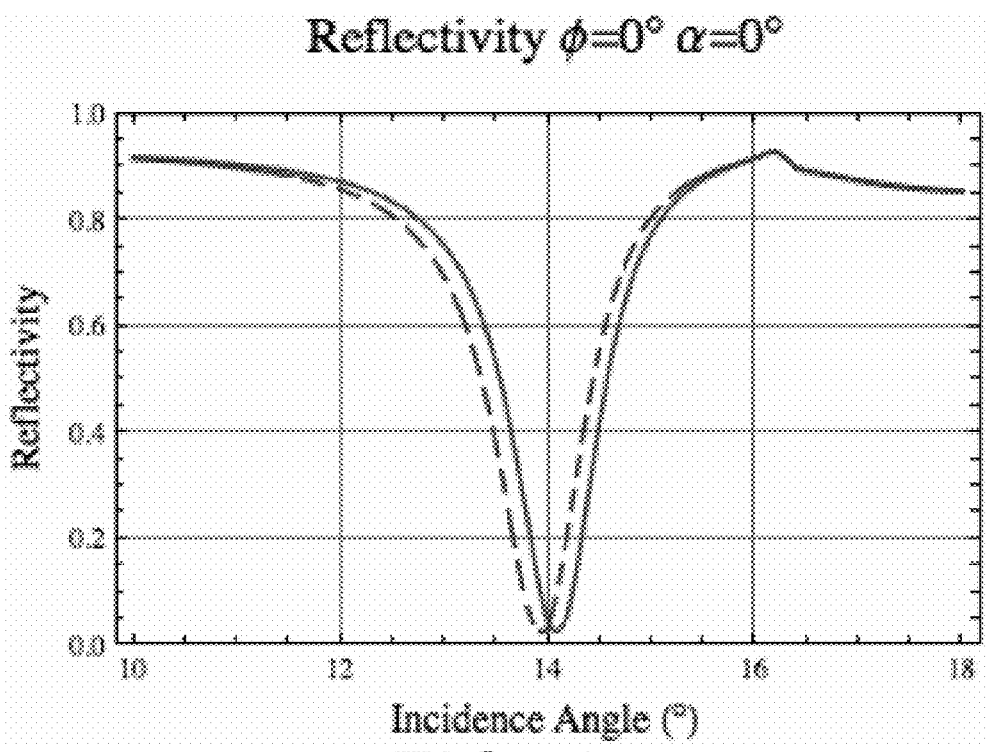
FIG. 4 shows simulated resonance angles for both uncoated and coated on un-rotated grating.

Changes in the optical and geometrical properties of the surface influence the SPPs dispersion law and therefore resonance conditions: Surface Plasmon Resonance sensors (SPR-sensors) work on this principle. If the metal surface is functionalized with a thin coating film, it is possible to measure film optical properties such as film thickness and refractive index, by analysing the changes on the resonance conditions, e.g. shift of resonance angle (as shown in FIG. 4.). There are different setups depending on the device configuration, e.g. angular-modulation (incident wavelength is fixed and the incidence angle is scanned), wavelength-modulation (incidence angle is fixed and wavelength is varied), intensity- and phase-modulations devices. Here our system is focused on angular interrogation, but the same description and methods are also valid in the case of wave length interrogation.

Even if PC-setup guarantees sensitivity and resolution slightly greater than GC-devices, an extreme precision in the prism alignment is required and the prism presence makes the device extremely cumbersome and difficult to miniaturize. On the other hand metallic gratings are suitable for miniaturization and integration in nano-devices.

Sensitivity Enhancement—Theoretical Description

Figure 5A:
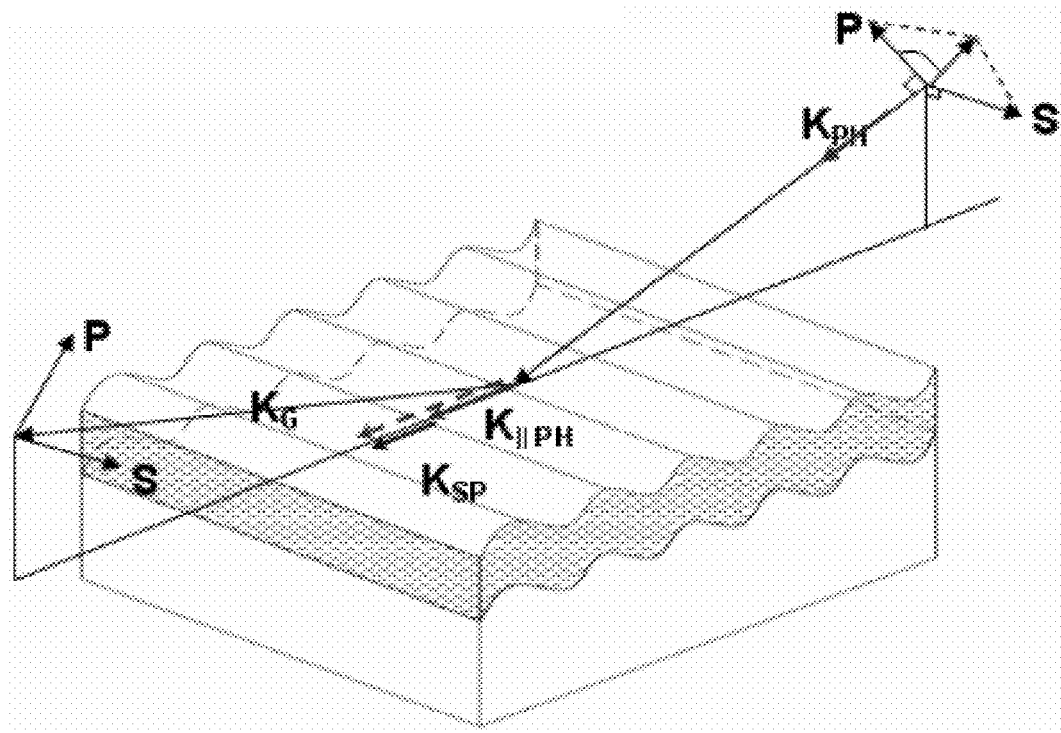
FIG. 5a-5b show the electromagnetic wave incident on either (a) un-rotated or (b) rotated diffraction grating. In the case of un-rotated grating, the incident photon and grating momentum are parallel to each others, resulting the excited surface plasmons are propagated along the same direction. However, in the case of rotated diffraction grating, the momentum of the grating is also rotated azimuthally, resulting the excited surface plasmons are propagated in different direction and can be controlled by grating rotation.
Figure 5B:
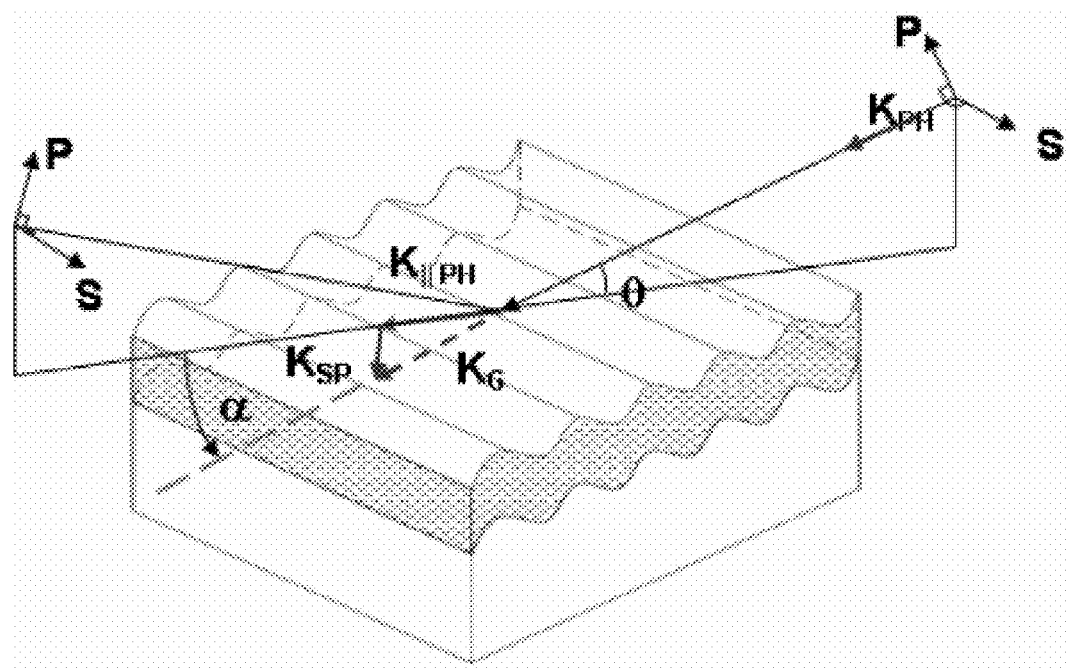

Experimental results and analytical works reveal that it is possible to improve sensitivity by grating rotation. In this case the scattering plane and the grating symmetry plane are no longer parallel and form an azimuthal angle Φ as shown in FIG. 5b Moreover, when grating azimuthal rotation exceeds a critical value $\Phi_c$, the reflectivity spectra changes dramatically. Two minima can be excited using a single wavelength.

Figure 6:
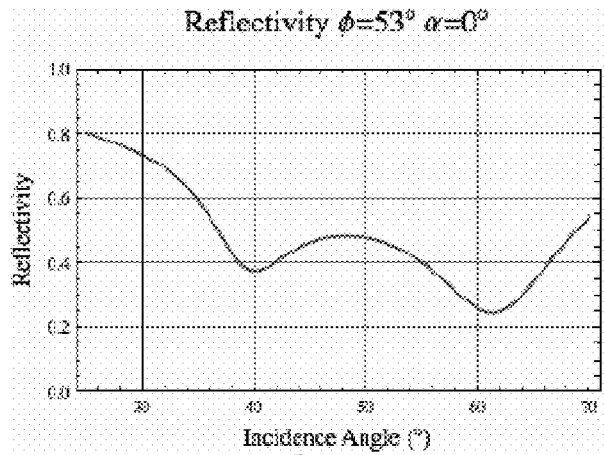
FIG. 6 is a simulated reflectivity spectrum when the grating azimuthal angle is grater than critical azimuthal angle $_c$.

A simulation of the reflectivity spectra is shown in FIG. 6. The condition for the appearance of two dips is explained in FIG. 8

Figure 7:
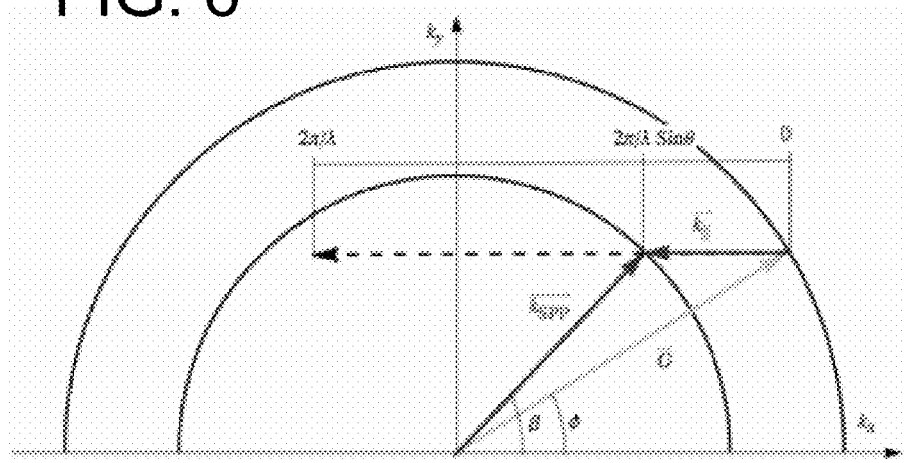
FIG. 7 is a The scheme represents wave-vector combination for one dip SPP reflectance excitation. The large (smaller) circle represents equi-magnitude $\vec{G}$ ($\vec{k}_{sp}$) vectors. The $k_{//}$ vector represents the projection of the photon wave-vector on the plasmonic crystal plane. The dotted lines vector represents the maximum length of the $k_{//}$ photon wave-vector in correspondence of a propagation of light tangent to the crystal plane. The $\Phi$ and $\beta$ angles represent the azimuthal orientation of the crystal momentum and the direction of propagation of the SPP.

We use the constructs shown in FIG. 7 to explain the SPP excitation in both un-rotated and rotated grating case.

Resonance condition is expressed in vector form on the grating plane and defined as:

$$\vec{k}_{SPP} = \vec{k}_{(||)} + [n\vec{G}], \quad (4)$$

where $\vec{G}$ is the grating vector, belonging to the grating plane and perpendicular to the diffraction pattern, with intensity G=2π/Λ, $k_{//}$ is the on-plane component of the incident wave-vector. In the analyzed samples, grating period Λ (typically 500 nm) is usually shorter than the illuminating wavelength and the resonance (4) condition is satisfied at diffraction order n=−1:

$$\vec{k}_{SPP} = \vec{k}_{(||)} - \vec{G}, \quad (5)$$

With such a choice of the reference frame that the scattering plane lies on the xz-plane, we have:

$$k_{SPP} \sin \beta = G \sin \Phi$$

$$k_{SPP} \cos \beta = G \cos \Phi - k \sin \Phi \quad (6)$$

From $\vec{G}$, the vector $k_{//}$ has origin, parallel to the $k_x$-axis and with intensity between two limit values:

$$0 \leq k_{II} = 2\frac{\pi}{\lambda}\sin\theta \leq \frac{2\pi}{\lambda}$$

The dotted line at the tip of the circle of radius $\vec{G}$, represents the x component of the photon wave-vector $k_{ph_x}$ that is the only component that participates in the SPP excitation. This line is scaled linearly in sinθ such that the full length of the line at the incident angle $\theta_{in}$ of 90° corresponds to the maximum value of $k_{ph_x}$. Because of the plus and minus conditions inherent in the wave-vector conservation requirement, all quadrants of the circle can be explored for plasmon resonances as long as the conservation is satisfied. However for symmetry reason only the $k_{ph_x}$ positive half space is shown. The intersection of the $k_{ph_x}$ horizontal line with the smaller $k_{sp}$ circle determines for which the wave-vector conservation is satisfied. This intersection also allows identification of the incident angle for SPP resonance excitation as well as the plasmon propagation direction β.

Figure 8:
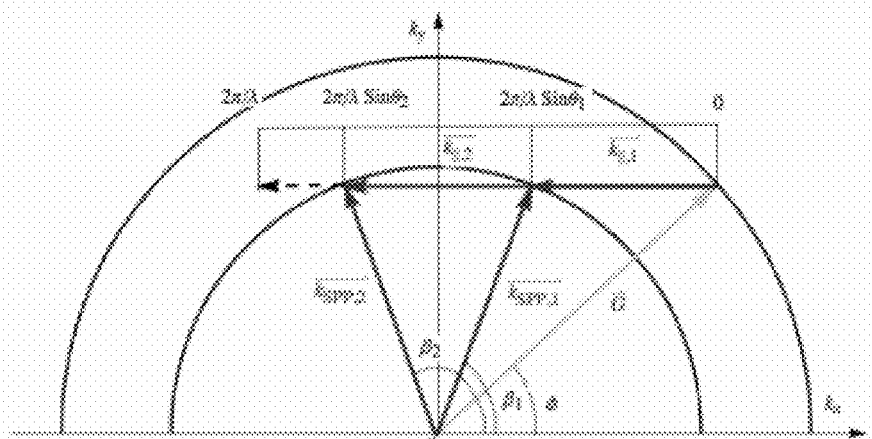
FIG. 8 is a vectorial resonance scheme of SPP excitation. Two dips configuration: the $k_{//}$ vector interests twice the $k_{spp}$ circle.

FIG. 7 shows the case in which the photon wave-vector can intersect the SPP circle only in the first quadrant but not the second, thus exciting only a single SPP. This is also true for Φ=0, where the grating, photon and SPP wave-vectors are all parallel. At fixed wavelength, resonance angle increases with azimuthal angle. At fixed wavelength, resonance angle increases with azimuthal angle. For azimuth values beyond a critical azimuthal angle, $\Phi_c$, it is possible that $k_{//}$ intersects the internal circle in two distinct points (FIG. 8). When the azimuth value $\Phi_c$ is reached, a second resonance dip appears at a greater incidence angle. This condition corresponds to the case $$k_{//} = \frac{2\pi}{\lambda}.$$

This condition explains the two resonance dips appearing in the reflectivity curve (FIG. 6). For increasing azimuthal values, the two dips approach each other till they merge into a single broad dip when the critical azimuth value $\Phi_{MAX}$ is reached. This is the condition for which the direction of propagation of the two KSPP are coincident and $\beta_1 = \beta_2 = 90°$. Beyond this value, resonance is no longer possible at any incidence angle.

When azimuth increases, the distance between these two points gets shorter and the two reflectivity dips begin to merge into a single dip when the vector $k_{//}$ is tangential to the internal circle. Beyond this configuration, no resonance is possible without a change of the incident wavelength, i.e. a change of the internal radius.

Figure 9:
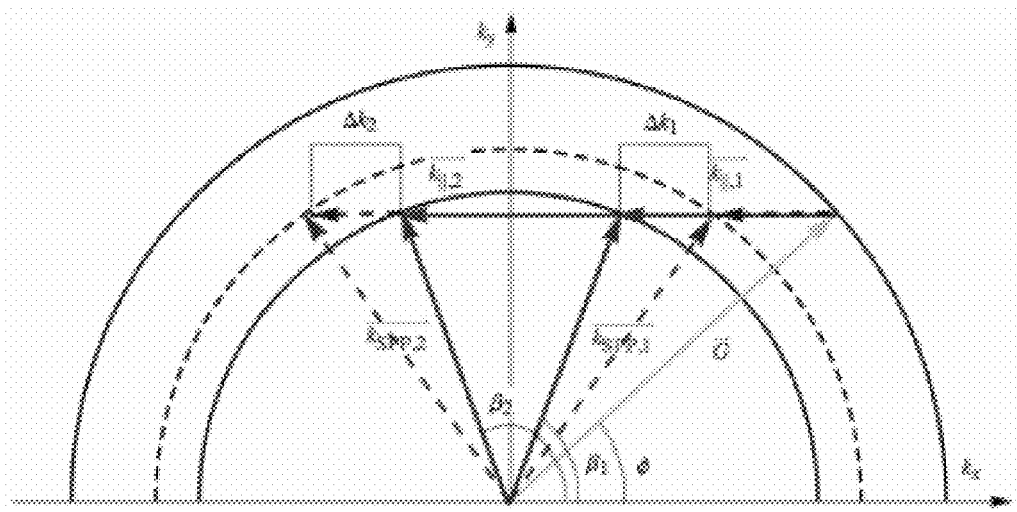
FIG. 9 is a vectorial resonance scheme of SPP excitation: response to a thin coating film.

We now consider the case of a thin film deposited on the plasmonic grating and the induced change of the effective refractive index of the surrounding medium. This can be the case for example of a homogeneous film deposited on the plasmonic grating, of the chemical functionalization of the gold surface with bonding analytes, or of a chemical variation of a previous deposited film due to molecules adsorption. As a consequence the SPP dispersion curve changes and therefore the internal circle radius changes accordingly. We shall consider the case of an increase of the index of refraction and therefore a reduction of the radius of the $K_{SPP}$ circle (as can be deduced by Eq. 1). The principle is also applicable in the case of a smaller refractive index. As a consequence, for a given azimuthal value, $k_{//}$ intersects the circle in a different point and the reflectivity curve shows a shift of the resonance angle. As shown in FIG. 9, when azimuth angle increases, resonance condition shift increases with respect the condition for $\Phi=0$ and therefore the response is improved.

Figure 10:
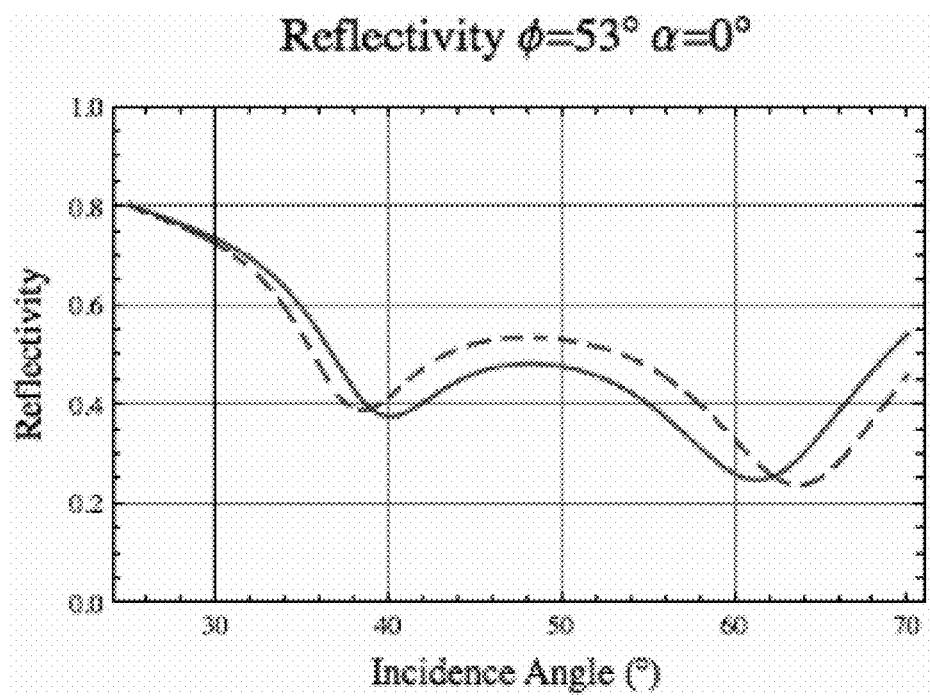
FIG. 10 is a comparison of reflectivity spectra obtained before (solid) and after (dashed) the deposition of a film on the uncoated plasmonic crystal.

A comparison between simulated reflectivity spectra before and after the deposition of a film on the uncoated plasmonic crystal is shown in FIG. 10.

The explanation of the increase of the sensitivity with the azimuthal angle can be obtained by a simple graphical analysis FIG. 9. The sensitivity is proportional to the variation of the wave vector, $\Delta k_1$, obtained by the variation of the radius change. $\Delta k_1$ is increasing with the azimuthal angle. For all the azimuthal angle greater than the critical one, it results that $\Delta k_1 = \Delta k_2$, namely the difference the wave vector variation for the two SPPs is the same.

This is a condition that is worth noting because it changes the perspective for the measurement. In a typical SPR configuration the changes of the index of refraction are evaluated with respect a spectrum of reference. It means that it is necessary to have a reference sample whose index of refraction must be changed. As mentioned previously, it can be done in several methods. In the case of double SPPs excitation, instead, the angular distance among the reflectivity dips can be converted in a wave vector distance and allow determining the refractive index of the film without reference. This internal reference system greatly simplifies the data collection and the data analysis.

Sensitivity Functional Dependence vs Azimuthal Angle

In the following section, we determine the analytical dependence of the sensitivity enhancement as a function of the azimuthal angle.

Grating sensitivity is defined by the variation of the measured quantity Y for a change in the refractive index n of the film:

$$S_{RI} = \frac{\partial Y}{\partial n} \quad (7)$$

where Y depends on the type of device: in the case of angular modulation $Y=\theta_{res}$, in the case of wavelength modulation $Y=\lambda_{res}$.

An analytical study provides a theoretical estimate of this improvement. At fixed azimuthal angle $\phi$ and incidence wavelength $\lambda$, we have the following expression for angular sensitivity:

$$S_{RI} = -\frac{1}{\cos\theta}\left(\frac{M}{n_0}\right)^3 \frac{\sqrt{\frac{1}{\Lambda^2} + \frac{\sin^2\theta}{\lambda^2} - \frac{2\cos\varphi\sin\theta}{\Lambda\lambda}}}{\frac{\cos\varphi}{\Lambda} - \frac{\sin\theta}{\lambda}} \quad (8)$$

where the resonance angle $\theta_{res}$ is given by:

$$S_{RI} = -\frac{1}{\cos\theta}\left(\frac{M}{n_0}\right)^3 \frac{\sqrt{\frac{1}{\Lambda^2} + \frac{\sin^2\theta}{\lambda^2} - \frac{2\cos\varphi\sin\theta}{\Lambda\lambda}}}{\frac{\cos\varphi}{\Lambda} - \frac{\sin\theta}{\lambda}} \quad (9)$$

M is given by $M=k_{SPP}/k$ and in first approximation the expression is the same as for flat interfaces (eq. 1):

$$M = \sqrt{\frac{n_{eff}^2 \varepsilon_M}{n_{eff}^2 + \varepsilon_M}}$$

Figure 11:
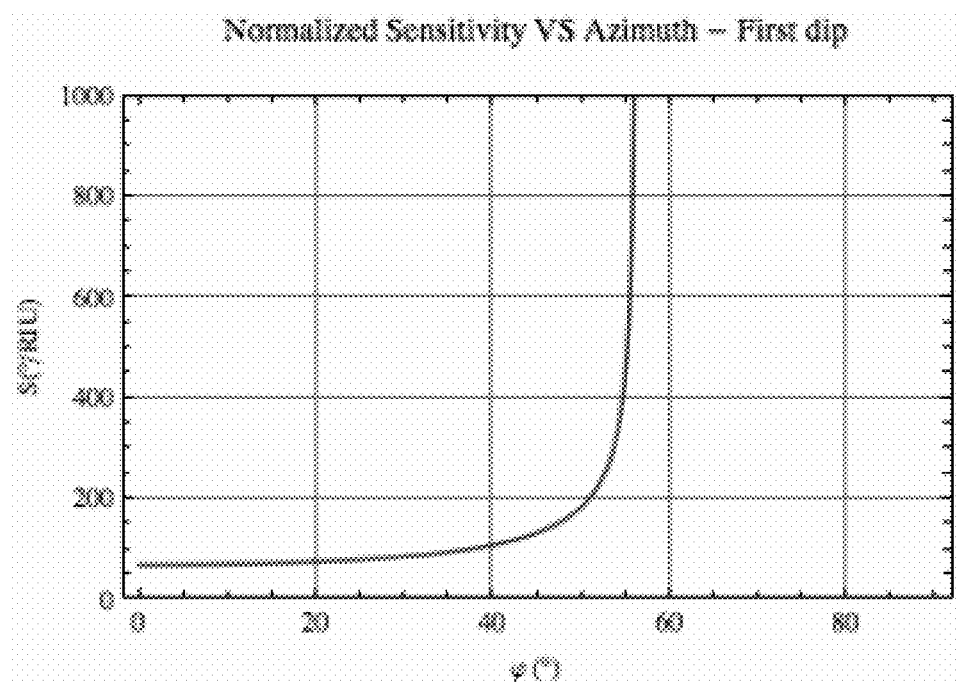
FIG. 11 is a first dip sensitivity (°/RIU) as a function of the azimuth angle (°) for a gold grating with period 510 nm, incident wavelength: 640 nm
Figure 12:
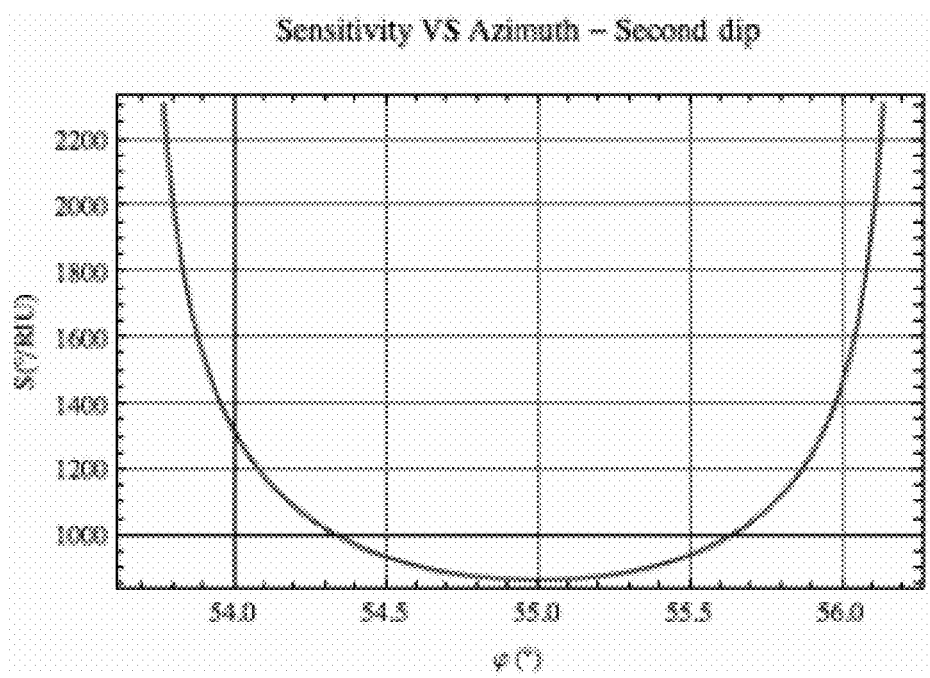
FIG. 12 is a second dip sensitivity(°/RIU) as a function of the azimuth angle (°) for a gold grating with period 510 nm, incident wavelength 640 nm
Figure 13:
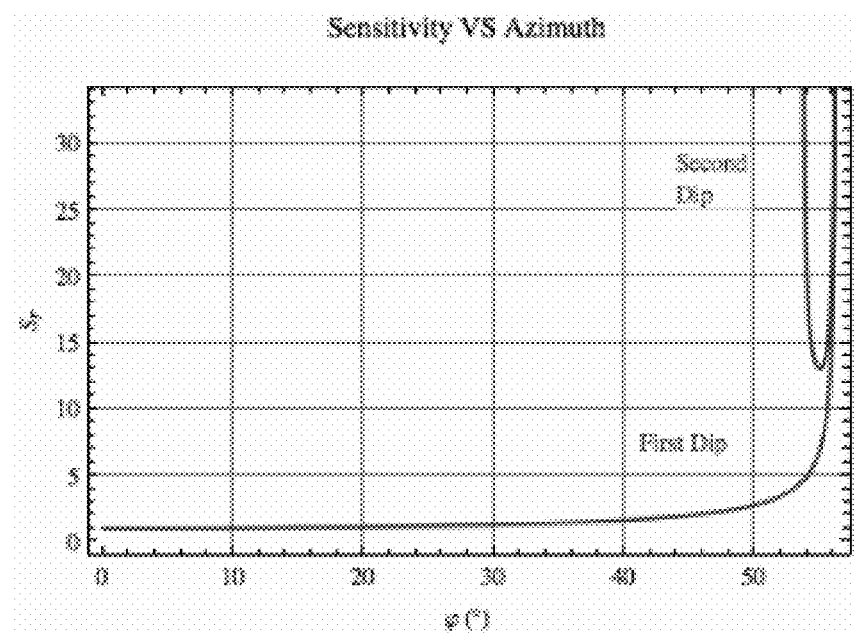
FIG. 13 is a values of sensitivity for the first and second dip normalized to the null-azimuth first dip sensitivity (classical mounting).

If we consider the first dip, sensitivity monotonically increases with azimuthal angle (FIG. 11). Second dip sensitivity instead, in the azimuthal range wherein the second dip exists, has a U-shape (FIG. 12), with values greater than the first dip ones (FIG. 13).

The following table compares angular shifts for PC setup and GC setup with and without grating rotation, after the deposition of a thin self-assembled monolayer of dodecanethiol ($C_{12}H_{25}SH$) on the metal surface (thickness 1.5 nm, $\varepsilon=2.205$):

TABLE 1

| Prism Coupling | $\Delta\theta_{RIS}(°)$ | | |
|---|---|---|---|
| | 0.118 | | |
| Au Grating (510 nm) | $\Delta\theta_{RIS}(°)$ (I dip) | $\Delta\theta_{RIS}(°)$ (II dip) | $\Delta\theta_{RIS}(\phi)/\Delta\theta_{RIS}(0)$ (Idip-IIdip) |
| 0° azimuth | 0.161 | | |
| 54.5° | 0.947 | 2.267 | 5.88-14.08 |
| 55.0° | 1.153 | 2.138 | 7.16-13.28 |
| 55.5° | 1.480 | 2.289 | 9.19-14.22 |
| 56.0° | 2.510 | 3.034 | 15.6-18.85 |
| 56.2° | 4.476 | 4.603 | 27.80-28.59 |

In the second dip sensitivity two singularities appear for the azimuthal angle close to the critical values $\Phi_c e \Phi_{MAX}$, which correspond respectively to the configurations wherein the second dip appears and the resonance disappears. In the first case the incidence angle is close to 90 degrees, $\cos\theta$ becomes null and sensitivity diverges. In the second case, as the vectorial scheme clearly explains, we have:

$$\phi = k_{\alpha\square||\square\alpha} \quad (11)$$

that means:

$$\varphi = \frac{2\pi}{(\sin\theta_{res})} \quad (12)$$

The denominator becomes null and sensitivity has a singularity. Although it is possible to get sensitivity 30-40 times higher than un-rotated case, technical and experimental limits invalidate measurements near to these values. When azimuth is close to $\Phi_c$, second dip resonance angle is great (>50°) and the angular spreading of the incident beam invalidates the reflectivity spectrum. When $\Phi$ approaches its maximum value, $\Phi_{MAX}$, the two resonance dips overlap and merge into a single broad dip which makes the two minima indistinguishable. Thus only the central range of the second dip sensitivity U-shape is exploitable in order to significantly improve the refractive index sensitivity by grating rotation. In this range the analysed structure gives a second dip sensitivity from 900 to 1100 °/RIU, about 15 times higher than un-rotated case. It is worth noting that the two resonance dips shift towards opposite directions. A more accurate way is by adding the shifts of the two dips together and in this case the total sensitivity is given by the sum of the single dip sensitivity:

$$S_{tot}=S_1+S_2$$

The combined sensitivity has a range from 1300 to 1700 °/RIU in the exploitable range. By normalizing with the sensitivity at null azimuth, the sensitivity of the combined 2 SPPs configuration is up to 24 times the conventional grating SPR sensor.

Polarization Role

Figure 14:
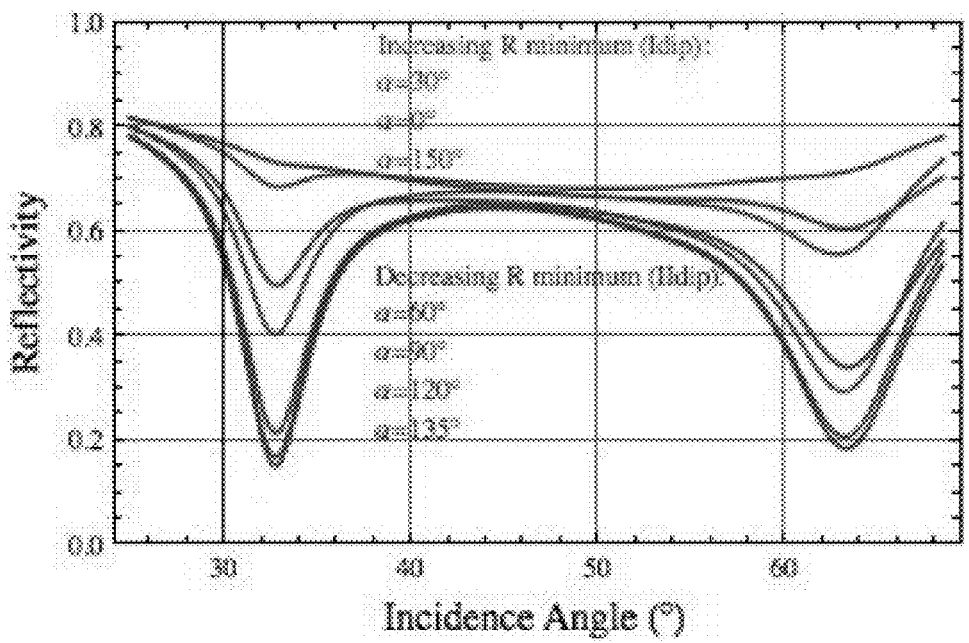
FIG. 14 is a simulated reflectivity spectrum at fixed azimuth (55°) and varying incidence polarization angle for a gold grating with period 510 nm and an incident wavelength of 640 nm
Figure 15:
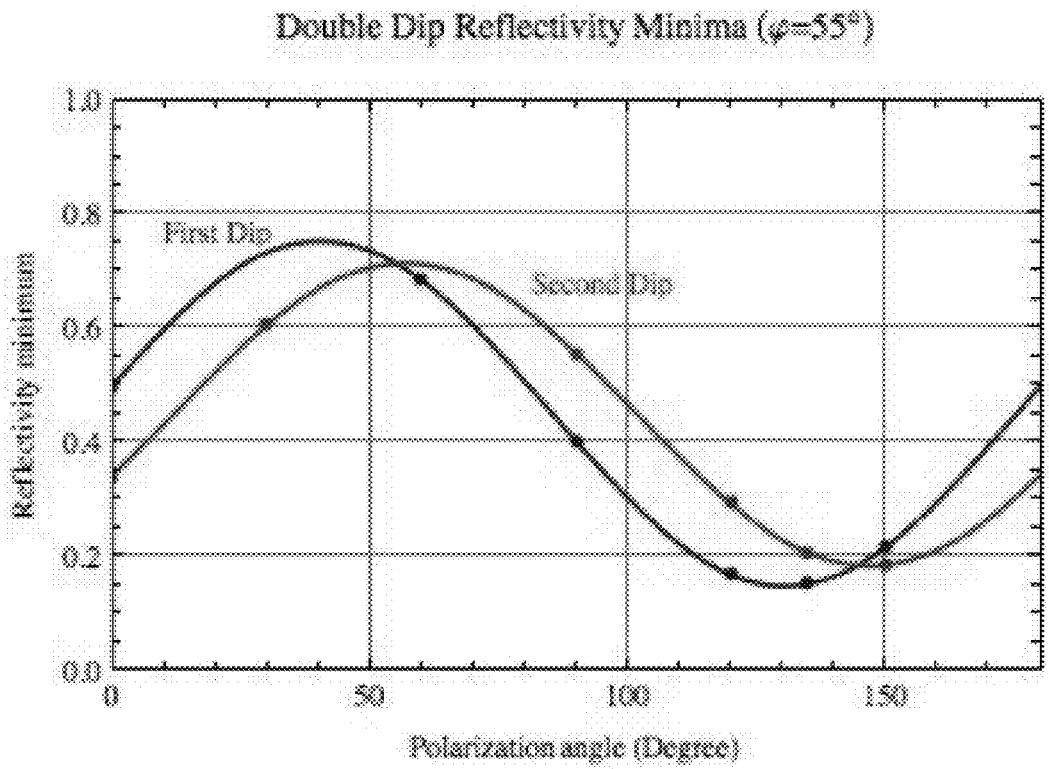
FIG. 15 is a reflectivity minimum dependency on polarization: simulation points and fitting curves for the two resonance dips

The symmetry breaking with grating rotation makes polarization have a fundamental role on surface plasmon polaritons excitation and the propagation of SPPs with a generic polarization is achievable. If we consider a TM-mode incident plane wave, sensitivity increases with azimuthal angle as we described in the previous sections, but reflectivity dip becomes shallower. For increasing azimuth angle in fact, p-polarization is no longer the most effective for SPP excitation and the coupling with illuminating light is less efficient. At a fixed non-null azimuthal angle $\phi$, reflectivity dip minimum value is obtained for a polarization $\alpha_{min}$ that is different from the TM-mode ($\alpha=0°$) (FIG. 14-15). Both experimental data and simulations show that at a fixed incidence azimuth, reflectivity minimum is a periodic function of polar 118 zation angle $\alpha$, which is best fitted by an harmonic function of twice the polarization angle (period 180°) (FIG. 15):

$$R_{min}=f_0-f_2 \cos(2\alpha+\alpha_0) \quad (13)$$

Where $f_0$, $f_1$ and the phase term $\alpha_0$ are fitting parameters that depend on grating geometry and materials and on the incidence conditions (wavelength and angles).

This behaviour can be easily explained with the use of the vectorial model and assuming symmetry principles. Grating 1D modulation restricts electron plasma oscillations to the grating symmetry plane formed by the versors $\hat{g}$ (parallel to the grating vector $\vec{G}$) and $\hat{n}$ (normal to the grating plane). Thus the only incident electric field component parallel to the symmetry plane is effective to SPP excitation and the orthogonal one represents the main contribution to reflectivity:

$$R \alpha |\hat{e}(\hat{g}\times\hat{n})|^2 \quad (14)$$

where $\hat{e}$ is the electric field versor.

This model gives an analytical expression for the calculation of the incident polarization angle $\alpha_{min}$ that optimizes the coupling with SPP modes at a fixed azimuthal angle $\phi$:

$$\tan\alpha_{min}=\cos\Theta_{res}\cdot\tan\phi \quad (15)$$

In the case of optimal polarization impinging the grating surface, the coupling strength is maximized and the reflectivity depth is minimized, thus in eq. (13) we have $\cos(2\alpha_{min}+\alpha_0)=1$ and we get the relation $\alpha_0=-2\alpha_{min}+2\max$, ($m\in\mathbb{Z}$). between the phase term and the optimized value.

Figure 16:
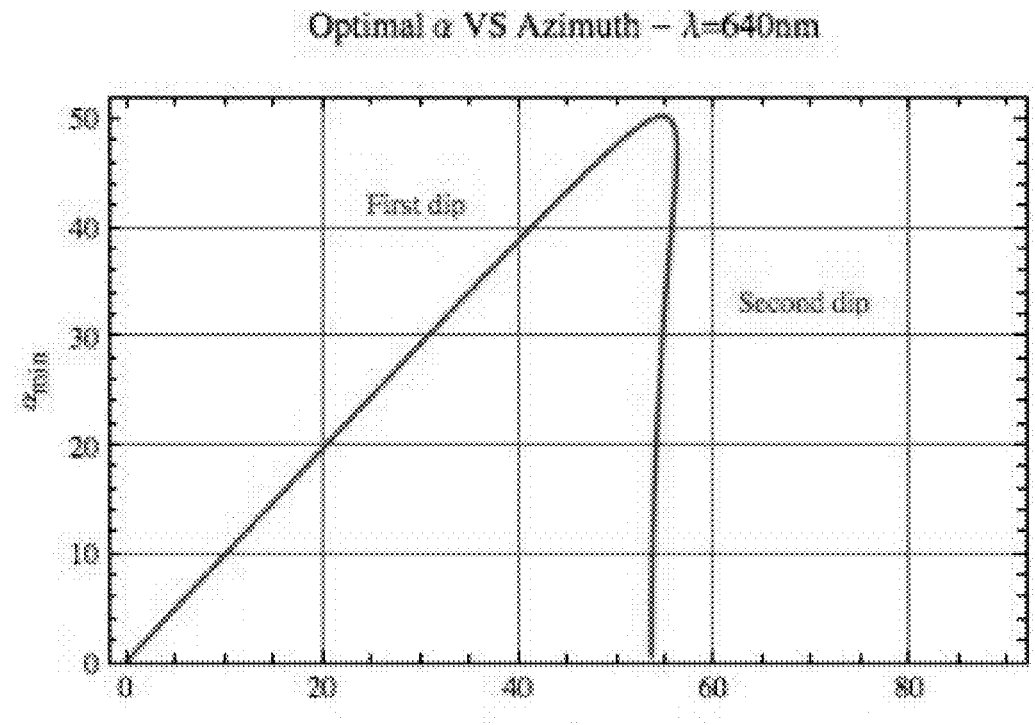
FIG. 16 is a optimal incident polarization as a function of azimuthal angle for a gold grating of period 510 nm and an incident wavelength of 640 nm

Since the optimal incident polarization angle depends on the incidence resonance angle, first and second dips show different values (FIG. 15-16). As it shown in FIG. 15 the optimal polarization incidence varies very sharply for the second dip. This means that at a fixed azimuthal angle for which two dips can be excited, namely for $\phi_c<\phi<\phi_{Max}$, a polarization scan allows to determine precisely the dips positions. In the following we shall describe a device that will use this type of scan for the determination of the reflectivity dips positions and therefore the refraction index determination.

If the grating surface is functionalized, the effective refractive index n of the dielectric medium changes and resonance conditions are different (eq. 9-10). As a consequence of the shift in the resonance angle $\theta_{res}$ for a fixed azimuth $\phi$, there is a change in the phase $\alpha_0$:

$$\Delta\alpha_0 = \frac{\partial\alpha_0}{\partial n}\Delta n \quad (16)$$

Where the phase sensitivity $$S_\alpha = \partial n_0/\partial n$$

is given by:

$$\frac{\partial\alpha_0}{\partial n} = \frac{2\sin\theta\tan\varphi}{1+\cos^2\theta-\tan^2\varphi}\frac{\partial\theta_{res}}{\partial n} \quad (17)$$

This result opens the route to a new grating-coupled SPR-configuration with polarization interrogation. In this setup the grating is rotated of an azimuthal angle $\phi$ which is kept fixed. The illuminating wavelength $\lambda$ is fixed and incoming light impinges on the grating at the resonance polar angle $\theta_{res}$. A rotating polarizer between source and sample-holder allows changing the polarization incident on the grating. A polarization scan of the illuminating light gives a harmonic dependence of the collected output signal according to eq. 13. If the grating surface is functionalized, a polarization scan, in the same and fixed conditions of incident wavelength $\lambda$ and angles $\phi$ and $\theta$, gives a harmonic output signal with a different phase parameter $\alpha_0$.

Once the system has been calibrated, it is possible to transduce the phase shift $\Delta\alpha_0$ into a refractive index change and thus into a quantification of grating surface functionalization or of molecule adsorption onto a sensitive coating layer. Since the dependence of the output signal on the polarization is a well known function, it is possible to get a very precise estimation of the phase term $\alpha_0$ from the fit with eq. 13.

Figure 17A:
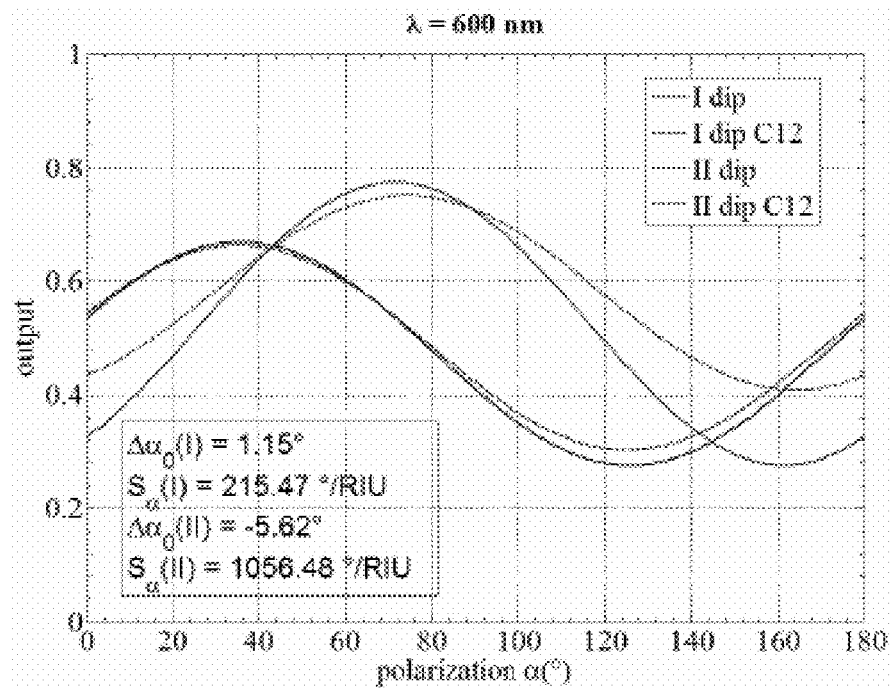
FIG. 17a-17c is a reflectivity in polarization scan for first (blue lines) and second (red lines) dips before (solid line) and after (dashed line) functionalization of the grating with a self-assembled monolayer of dodecanethiol (C12) for fixed azimuth angle =51° and wavelengths =600 nm (a), 620 nm (b) and 635 (c-merged dips). Experimental data for light impinging on a gold grating with period 505 nm.
Figure 17B:
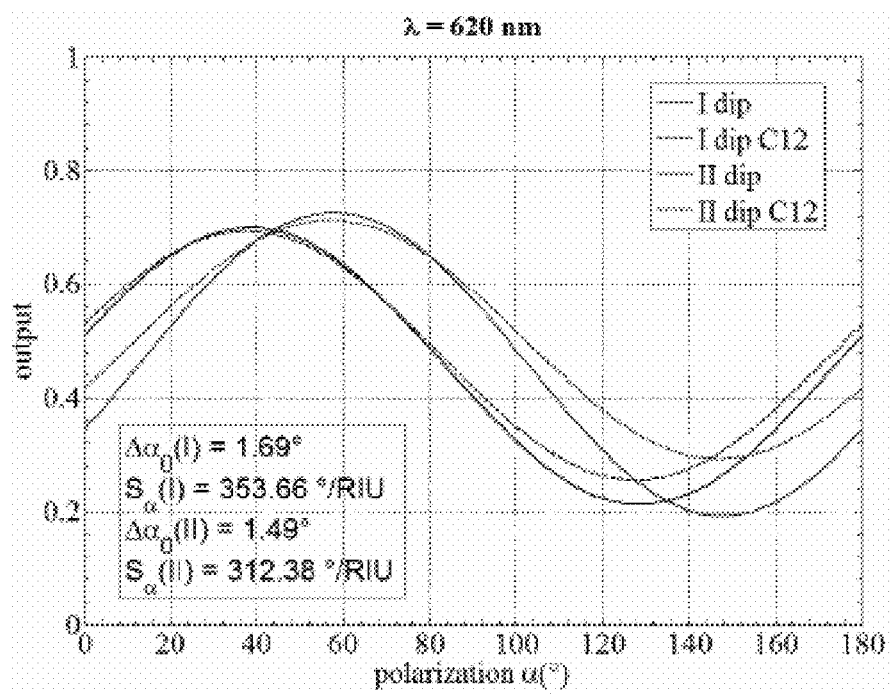
Figure 17C:
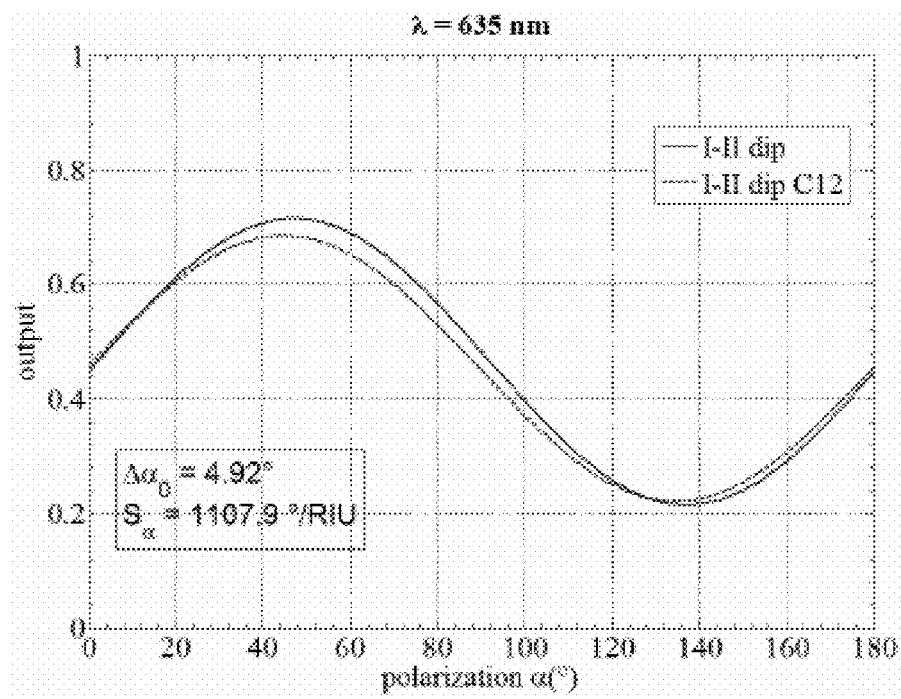

The following table collects the results of SPR-analysis with polarization scan related to the deposition of a thin self-assembled monolayer of dodecanethiol ($C_{12}H_{25}SH$-thickness 1.5 nm, $\in=2.205$) on the grating metal surface. The grating was azimuthally rotated and kept fixed at such an azimuth-angle value that provides the excitation of double SPPs in the considered wavelength range (in our case $\phi=51°$, $\lambda=600$-635nm). For each wavelength, a polarization scan was performed in the range 0-180° in correspondence of the resonance polar angle $\theta_{res}$ both for first and second dip. Polarization scans are reported in FIGS. 17.a-b-c and the measured phase shifts $\Delta\alpha$ after functionalization is collected in table 2.

Three cases or interest are reported:
  a. $\lambda=600$ nm (FIG. 17a): the two resonance dips are perfectly distinguishable.
  b. $\lambda=620$ nm (FIG. 17b): the two resonance dips are near to merge and interfere.
  c. $\lambda=635$ nm (FIG. 17c): the two resonance dips are merged into a single broad dip.

TABLE 2

| λ (nm) | Δn | Δα₀(°) | σ_Δ(°) | S_α(sensitivity-°/RIU) | σ_n(resolution-RIU) |
|---|---|---|---|---|---|
| 600 (I) | 0.00532 | 1.1463 | 0.0026 | 215.47 | 12.0e−6 |
| 600 (II) |  | −5.6205 | 0.0023 | 1056.48 | 2.2e−6 |
| 620 (I) | 0.00478 | 1.6905 | 0.0015 | 353.66 | 4.2e−6 |
| 620 (II) |  | 1.4932 | 0.0015 | 312.38 | 4.8e−6 |
| 635 (I-II) | 0.00444 | 4.9191 | 0.0018 | 1107.91 | 1.6e−6 |

Modeling refractive index change $\Delta n$ with an effective medium approximation, it is possible to estimate the phase sensitivity $S_\alpha$ which corresponds to a phase shift $\Delta \alpha$. Moreover it is possible to calculate the refractive index resolution $\sigma_n$:

$$\sigma_n = \frac{\sigma_\alpha}{S_\alpha} \quad (18)$$

where $\sigma_\alpha$ is the phase resolution, which strictly depend on the output signal (e.g. polarization step size, signal-to-noise ratio) and on the analysis procedure (signal-transduction process and data-analysis algorithm).

As table 2 shows, the best performances in resolution and sensitivity are obtained either for the second dip in the configuration wherein the two resonances are well distinguishable, or after merging in the case of a single broad dip. Refractive index changes of order $10^{-6}$ RIU are easily detectable and the resolution can be further improved to $10^{-7}$-$10^{-8}$ by increasing the number of the collected points during the polarization scan or by reducing output noise.

The SPR technique based on polarization modulation with azimuthal rotation reveals a great robustness and tolerance in system alignment. Since every point of reflectivity dip changes with the same phase during polarization scan, it is not necessary to perfectly set the polar angle at the SPP resonance value $\theta_{res}$. Moreover the possibility of analysing the merged dip phase shift, which revealed better performance in sensitivity, further assures a greater tolerance because of its wide spread in angle.

Figure 18:
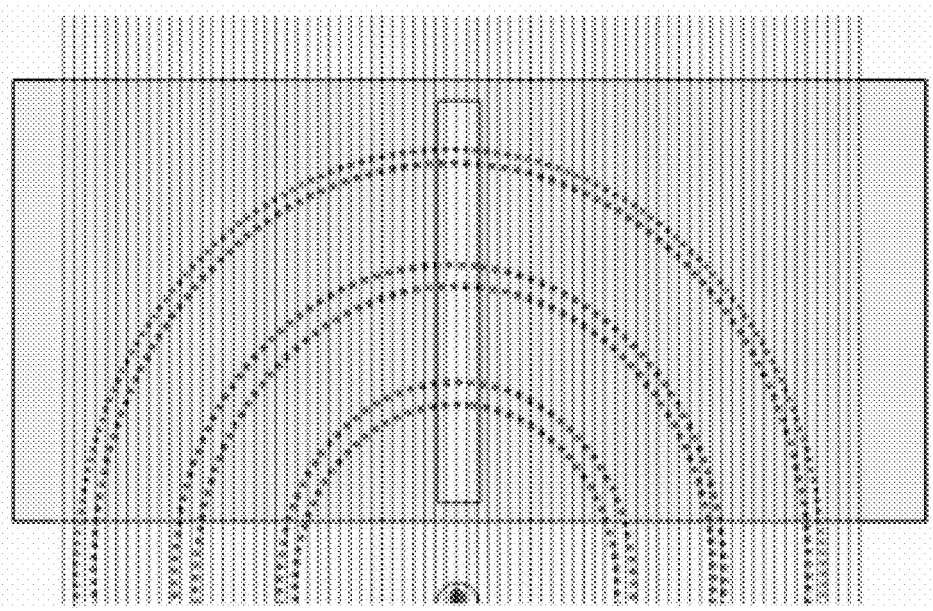
FIG. 18 shows the schematic of the sensor chips. The chip consists of diffraction grating with sinusoidal profile fabricated using interference lithography on a silicon or glass substrate and evaporated with Ag and Au. On back of the diffraction grating, a microfluidic channels is patterned, and interest analytes can be flowed through these channels. A small slit is located on top of the grating and control the active area (light that are able to incident on the diffraction grating).
Figure 19:
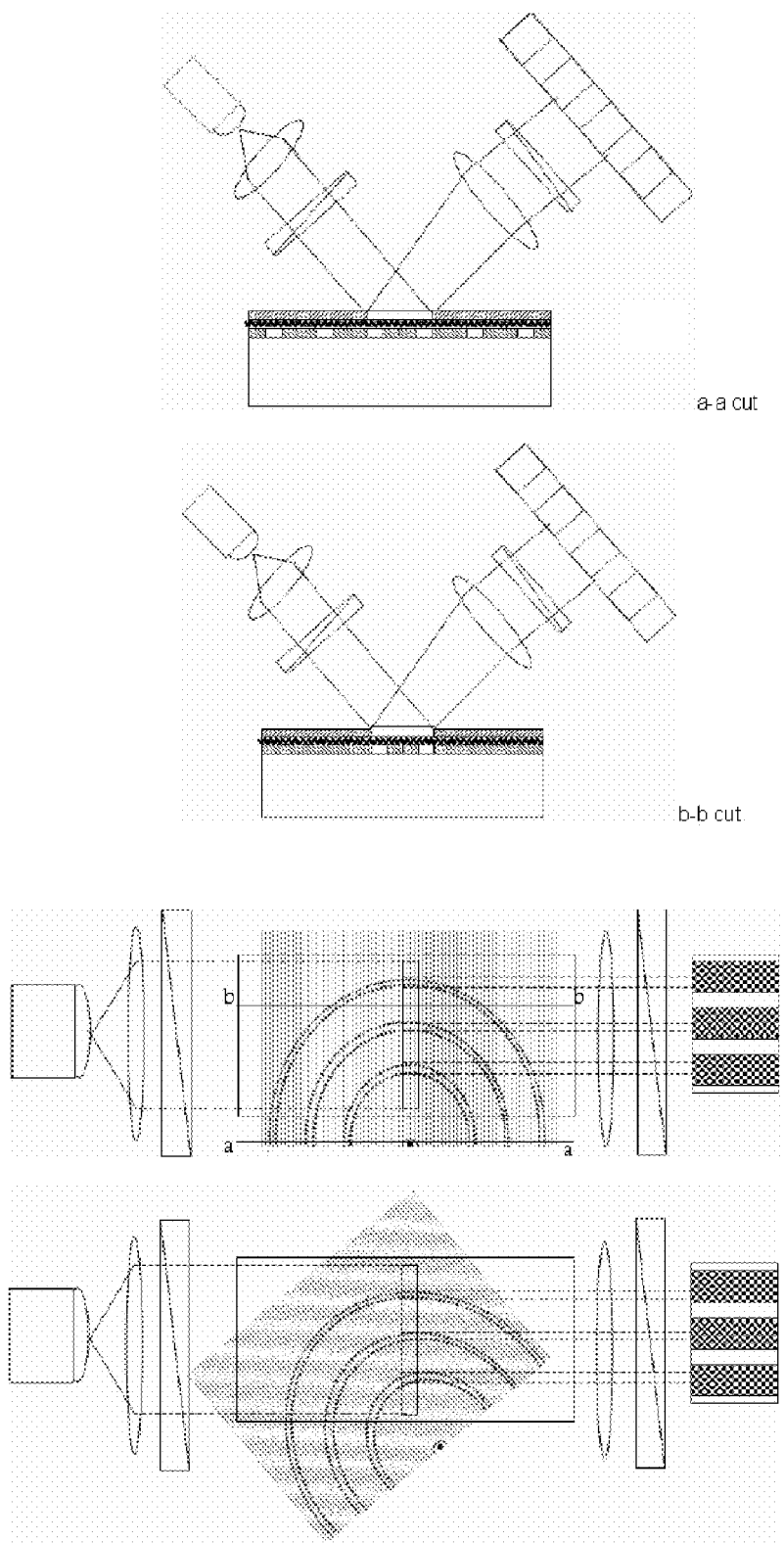
FIG. 19 is a Shows the SPR sensor system in (a) & (b) side view with a-a cut and b-b cut respectively and (c) & (d) top view with un-rotated and rotated grating. The light is emitted from a monochromatic light source, passing through a converging lens and focus on a slit which located on top of diffraction grating. The polarization of the incident light can be controlled using a polarizer. The diffracted beam from slit is collected by a CCD, and polarized using a polarizer.

One embodiment, as shown in FIGS. 18 and 19, includes the following elements:

A plasmonic crystal grating generated on a glass or another transparent flat and rigid substrate. It can have either a sinusoidal or a digital profile or any intermediate profile. It can be generated by interference lithography, or by imprinting replica or by electron beam lithography or any other suitable lithography system. Typical lattice period will be in the range of 200-2000 nm and with amplitude of 10-500 nm.

A micro array of plasmonic grating distributed along a line. It is composed of a large area of grating (more than 40×40 mm2) on top of which some circular microfluidic channels have been patterned. The microfluidic channels are made of transparent material and sealed on a covering glass. On the back of the glass is the grating. This element comprised with the grating is now on called SPPchip.

A system for the rotation of SPPchip, called rotating stage. On top of the SPPchip an optical screen defines a rectangular window.

A linear light beam source whose cross section is a small circle that emits white beam from visible to near infrared.

An optical system comprised of a collimator lens and a polarizer. The collimator lens first collimates the light on the rectangular window, the polarizer is controlled the polarization angle of the incident wavelength. The respective angles of rotation are called Pinc and Prefl.

A simple grating monochromatic or a multi-diffractive grating that generates a wavelength division multiplexing (WDM). In this second case a polychromatic light beam will made incident onto a special metallic grating with a grating profile composed of multiple harmonics.

The optical system for the collection of the diffracted light is using a linear CCD system. The system can detect light at different wavelengths.

A polarizer is required before diffracted light collected by CCD system.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A surface plasmon resonance sensor in grating coupling configuration, comprising:
    a plasmonic crystal grating, with a selected one of a sinusoidal profile or digital profile;
    a system of microfluidic channels made of a transparent material and placed on top of the grating, which element is referred to as an SPPchip, that is configured to allow the flow of an analyte therethrough;
    a light source that emits a monochromatic light beam that induces surface plasmon polariton excitation, hereafter called a first beam, which impinges on the SPPchip and is thereby reflected, into a second beam, which identifies with the first beam as a scattering plane;
    a first polarizer, disposed between the light source and the SPPchip, that is configured to rotate so as to control polarization of the first beam;
    a second polarizer in the path of the second beam;
    a rotating stage upon which the SPPchip is placed and configured to rotate azimuthally and so as to control angle of rotation of the scattering plane, thereby controlling an azimuthal angle, which is set at a non-null value during analysis; and
    an optical system for detecting the second beam thereby detecting information about the analyte, the optical system including a CCD system.

2. A surface plasmon resonance sensor in grating coupling configuration, comprising:
    a plasmonic crystal grating, with a selected one of a sinusoidal profile or digital profile;
    a system of microfluidic channels made of a transparent material and placed on top of the grating, which element is referred to as an SPPchip, that is configured to allow the flow of an analyte therethrough;
    a light source that emits a light beam that induces surface plasmon polariton excitation, hereafter called a first beam, which impinges on the SPPchip and is thereby reflected, into a second beam, which identifies with the first beam as a scattering plane;
    a first polarizer, disposed between the light source and the SPPchip, that is configured to rotate so as to control polarization of the first beam;

a second polarizer in the path of the second beam;
a rotating stage upon which the SPPchip is placed and configured to rotate azimuthally and so as to control angle of rotation of the scattering plane, thereby controlling an azimuthal angle, which is set at a non-null value during analysis; and
an optical system for detecting the second beam thereby detecting information about the analyte, the optical system including a CCD system,
wherein the light source emits a polychromatic beam.

3. A system as claimed in claim 1, wherein the azimuthal angle is fixed at a non null value, wherein the first beam has a wavelength that is fixed, wherein the first beam has an incidence angle that is fixed, the second beam has a polarization that is fixed and only the first beam has a variable polarization.

4. A system as claimed in claim 1, wherein the wavelength of the first beam is fixed, wherein the first beam has an incidence angle that is fixed, wherein the first beam has a polarization that is fixed and only the azimuthal angle is variable.

5. A surface plasmon resonance sensor in grating coupling configuration, comprising:
a plasmonic crystal grating, with a selected one of a sinusoidal profile or digital profile;
a system of microfluidic channels made of a transparent material and placed on top of the grating, which element is referred to as an SPPchip, that is configured to allow the flow of an analyte therethrough;
a light source that emits a light beam that induces surface plasmon polariton excitation, hereafter called a first beam, which impinges on the SPPchip and is thereby reflected, into a second beam, which identifies with the first beam as a scattering plane;
a first polarizer, disposed between the light source and the SPPchip, that is configured to rotate so as to control polarization of the first beam;
a second polarizer in the path of the second beam;
a rotating stage upon which the SPPchip is placed and configured to rotate azimuthally and so as to control angle of rotation of the scattering plane, thereby controlling an azimuthal angle, which is set at a non-null value during analysis; and
an optical system for detecting the second beam thereby detecting information about the analyte, the optical system including a CCD system,
wherein the azimuthal angle is fixed at a non null value, wherein the first beam has a fixed polarization angle, wherein the first beam angle has a fixed angle of incidence, and wherein the first beam has a polychromatic wavelength.

* * * * *